(12) United States Patent
Huang et al.

(10) Patent No.: US 10,744,403 B2
(45) Date of Patent: Aug. 18, 2020

(54) METHOD AND APPARATUS FOR ADJUSTING GAME SCENE

(71) Applicant: Anhui Huami Information Technology Co., Ltd., Hefei, Anhui (CN)

(72) Inventors: Wang Huang, Hefei (CN); Hui Wang, Anhui (CN)

(73) Assignee: Anhui Huami Information Technology Co., Ltd., Hefei, Anhui (CN)

( * ) Notice: Subject to any disclaimer, the term of this patent is extended or adjusted under 35 U.S.C. 154(b) by 128 days.

(21) Appl. No.: 16/155,316

(22) Filed: Oct. 9, 2018

(65) Prior Publication Data
US 2019/0038965 A1 Feb. 7, 2019

Related U.S. Application Data

(63) Continuation of application No. 15/014,574, filed on Feb. 3, 2016, now abandoned.

(30) Foreign Application Priority Data

Feb. 10, 2015 (CN) .......................... 2015 1 0070750

(51) Int. Cl.
*A63F 13/69* (2014.01)
*A63F 13/212* (2014.01)
*A61B 5/16* (2006.01)
*G06F 3/01* (2006.01)
*A61B 5/024* (2006.01)

(52) U.S. Cl.
CPC ........ *A63F 13/212* (2014.09); *A61B 5/02438* (2013.01); *A61B 5/165* (2013.01); *A63F 13/69* (2014.09); *G06F 3/015* (2013.01)

(58) Field of Classification Search
CPC .... A63F 13/212; A63F 13/69; A61B 5/02438; A61B 5/165; G06F 3/015
See application file for complete search history.

(56) References Cited

U.S. PATENT DOCUMENTS

2006/0224046 A1* 10/2006 Ramadas ............. A61B 5/0002
600/300
2010/0304864 A1* 12/2010 Johnson ............... A61B 5/0402
463/36

* cited by examiner

*Primary Examiner* — Corbett B Coburn
(74) *Attorney, Agent, or Firm* — Young Basile Hanlon & MacFarlane, P.C.

(57) ABSTRACT

Methods and apparatuses for adjusting a game scene are set forth herein. The method includes receiving heart rate information of a user, wherein the user wears the computing device to play the game, and based on the received heart rate information of the user, adjusting at least one element in the game scene of the game. By using a smart wearable device to acquire the heart rate information of the user playing the game, the game scene of the game can be adjusted according to the heart rate information. Therefore, the game can be made to be more interesting by receiving multi-dimensional interaction information of the user.

14 Claims, 5 Drawing Sheets

METHOD AND APPARATUS FOR ADJUSTING GAME SCENE

CROSS-REFERENCE TO RELATED APPLICATION

This application is a continuation of U.S. patent application Ser. No. 15/014,574, filed on Feb. 3, 2016, which claims priority to Chinese Patent Application No. CN 201510070750.0, filed on Feb. 10, 2015, the entire disclosures of which are herein incorporated by reference.

TECHNICAL FIELD

The present disclosure generally relates to computer game technologies, and more particularly, to methods and apparatuses for adjusting game scenes.

BACKGROUND

With developments in technologies, electronic games based on devices such as computers, tablet computers and cell phones become more and more popular and convenient. In addition, game consoles extend the popularity of games as well, and provide more interesting game functions by introducing contents of motion sensing and computer vision into game devices.

A virtual game is often controlled by controls input by a user. For example, the user can operate a game controller, or the game can identify user gestures and motions, by which more vivid and involving games can be made.

SUMMARY

Disclosed herein are implementations of methods and apparatuses for adjusting game scenes.

In one aspect, the present disclosure includes a system for playing a game and adjusting one or more elements of a game scene within the game. The system comprises a wearable device, a game console, and a game server. The wearable device includes one or more sensors for receiving heart rate information of a user while the user is playing the game. The game console is configured for wireless communication with the wearable device and includes a first processor and a first memory. The game server is in communication with the game console and includes a second processor and a second memory. The game is implemented using the game console and the game server. The first processor of the game console executes instructions stored in the first memory of the game console to: determine whether the user is wearing the wearable device; responsive to a determination that the user is wearing the wearable device, establish a connection with the wearable device; use the connection established with the wearable device to transmit a request for the heart rate information to the wearable device; receive the heart rate information from the wearable device responsive to the request for the heart rate information; transmit the heart rate information to the game server; receive instructions for adjusting the one or more elements of the game scene from the game server based on the prior transmission of the heart rate information to the game server; and adjust the one or more elements of the game scene according to the instructions for adjusting the one or more elements of the game scene. The second processor of the game server executes instructions stored in the second memory of the game server to: receive the heart rate information from the game console; map the heart rate information to a timeline of the user in the game, the timeline corresponding to the game scene; determine one or more emotion fluctuations of the user based on variations within the heart rate information over the timeline to which the heart rate information is mapped; generate the instructions for adjusting the one or more elements of the game scene according to the one or more emotion fluctuations of the user; and transmit the instructions for adjusting the one or more elements of the game scene to the game console.

In another aspect, the present disclosure includes a method for adjusting one or more elements of a game scene based on heart rate information of a user of a wearable device. The method comprises: determining, by a game console configured for communication with the wearable device, whether the user is wearing the wearable device, the wearable device including one or more sensors for receiving the heart rate information of the user; responsive to determining that the user is wearing the wearable device, causing the game console to connect to the wearable device; using a connection established between the game console and the wearable device to transmit, from the game console, a request for the heart rate information to the wearable device; receiving, by the game console, the heart rate information from the wearable device responsive to the request for the heart rate information; transmitting, from the game console, the heart rate information to a game server in communication with the game console, wherein a game including the game scene is run at least in part using the game server; mapping, by the game server, the heart rate information with a timeline of the user in the game, the timeline corresponding to the game scene; determining, by the game server, one or more emotion fluctuations of the user based on variations within the heart rate information over the timeline to which the heart rate information is mapped; generating, by the game server, instructions for adjusting the one or more elements of the game scene according to the one or more emotion fluctuations of the user; receiving, by the game console, the instructions for adjusting the one or more elements of the game scene from the game server; and adjusting, by the game console, the one or more elements of the game scene according to the instructions for adjusting the one or more elements of the game scene.

In yet another aspect, the present disclosure includes integrated circuit comprising a processor. The processor is configured to execute instructions to: cause a transmission, to a wearable device, of a request for heart rate information of a user of the wearable device, wherein the user uses the wearable device to play a game; receive the heart rate information of the user from the wearable device responsive to the request for the heart rate information of the user, wherein the wearable device uses one or more sensors to receive the heart rate information; map the heart rate information with a timeline of the user in the game, wherein the timeline corresponds to a game scene within the game; determine one or more emotion fluctuations of the user based on variations within the heart rate information over the timeline to which the heart rate information is mapped; and adjust one or more elements of the game scene within the game according to the one or more emotion fluctuations.

The embodiments or implementations can be configured as executable computer program instructions stored in computer storages such as memory.

BRIEF DESCRIPTION OF THE DRAWINGS

The description here makes reference to the accompanying drawings wherein like reference numerals refer to like parts throughout the several views, and where.

DETAILED DESCRIPTION

Example implementations of the present disclosure will be described below with reference to the accompanying drawings. The same numbers across the drawings set forth in the following description represent the same or similar elements, unless differently expressed. The implementations set forth in the following description do not represent all implementations or embodiments consistent with the present disclosure; on the contrary, they are only examples of apparatuses and methods in accordance with some aspects of this disclosure as detailed in the claims.

Figure 1:
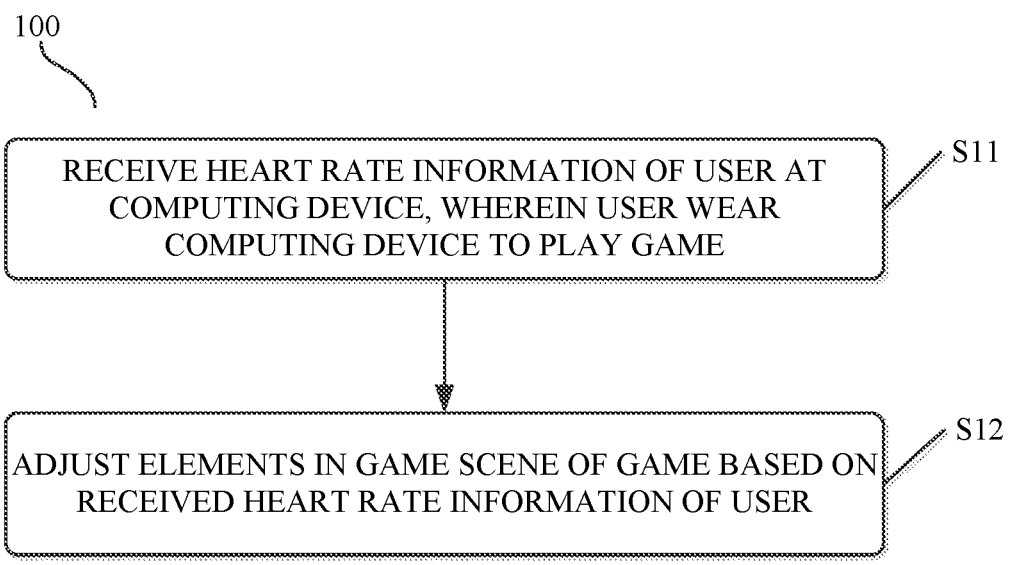
FIG. 1 is a flowchart of an example method for adjusting a game scene according to implementations of this disclosure.

FIG. 1 is a flowchart of a method for adjusting a game scene which can be implemented in a game console or game software, according to implementations of this disclosure is shown. The method includes operations set forth in the following description.

At operation S11, heart rate information of a user who wears a computing device to play a game is received by the computing device.

At operation S12, in response to the received heart rate information of the user, in a game scene of the current game played by the user are adjusted based on one or more elements.

In some implementations, based on the received heart rate information in the user, the game scene of the current game played by the user can be adjusted based on one or more elements in the following: a game character design, a screen background, a game plot or item purchase. The item can be, for example, a game object or prop.

In some implementations, heart rate information of the user playing the game can be received using a computing device, for example, a "smart" wearable device such as a smart wristband configured with a heart rate sensor. The receiving herein can include, for example, actions of receiving, obtaining, determining, acquiring, identifying or collecting information from a source such as a sensor. Based on the heart rate information, a corresponding game scene can be adjusted or set up. For example, when the received heart rate of the user suddenly accelerates, it can be determined that the user is excited. In response to the excitement of the user, the game character design, for example, facial color, hair style and dressing, the screen background, for example, color rendering, and the game plot can be changed, or appropriate game props can be released to stimulate user purchase. Therefore, the game can be made to be more interesting by receiving multi-dimensional interaction information of the user.

Figure 2:
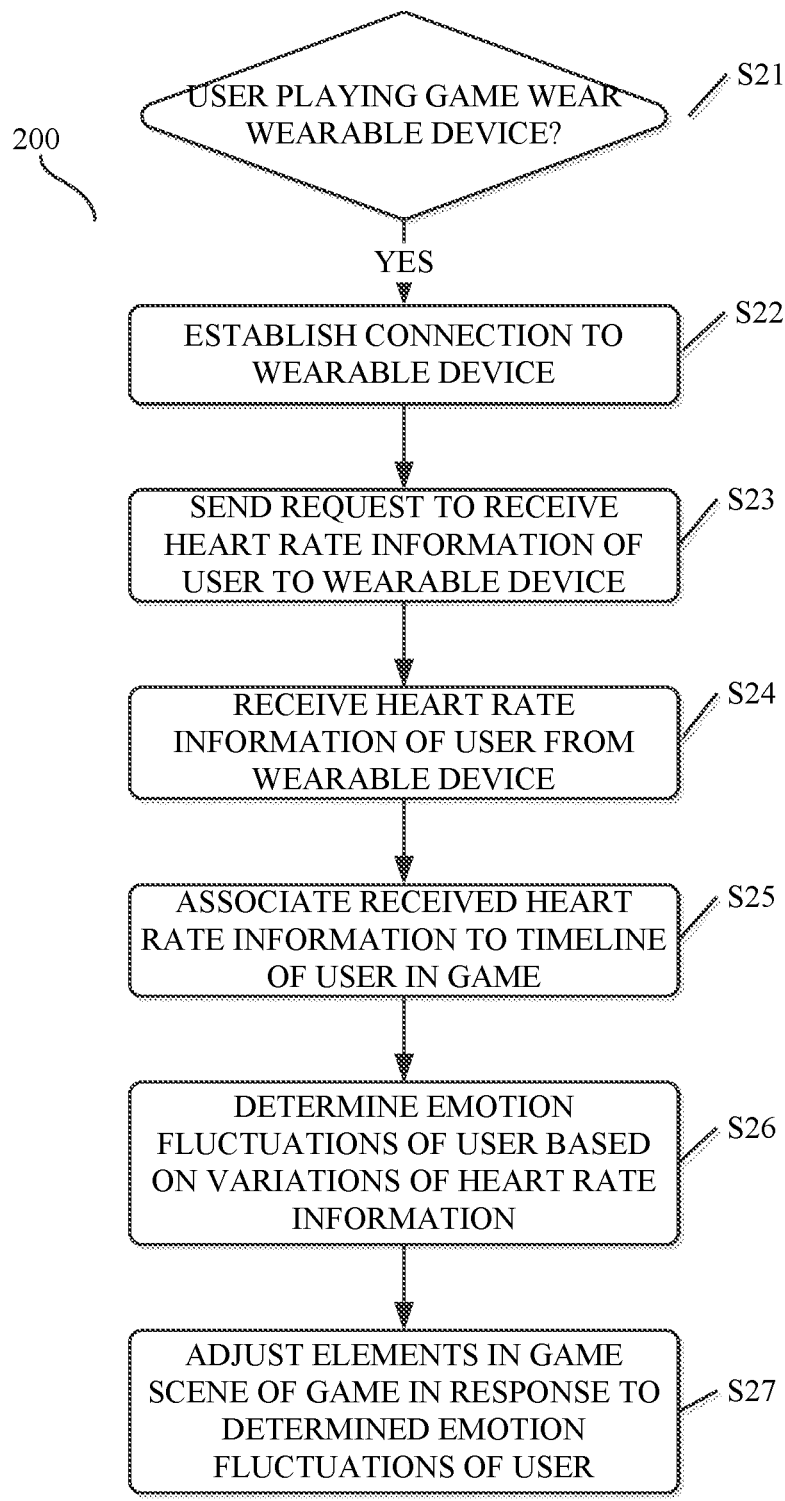
FIG. 2 is a flowchart of another example method for adjusting a game scene according to implementations of this disclosure.

FIG. 2 is a flowchart of another example method for adjusting a game scene as an example, according to implementations of this disclosure. In some implementations, based on received heart rate information of a user, emotion fluctuations of the user can be determined. The method includes operations set forth in the following description.

At operation S21, it is determined that whether the user playing a game wears a wearable device; if the user wears the wearable device, this process proceeds to operation S22; otherwise, this process ends.

At operation S22, a connection to the wearable device worn by the user is established.

At operation S23, a request to receive the heart rate information of the user is sent to the wearable device.

In some implementations, a request to receive the heart rate information of the user playing the game can be sent directly to the wearable device. In other implementations, for example, the wearable device can transmit, (e.g., upload), the heart rate information to a storage in an accessible network, and a game console or game software can receive, (e.g., download), the heart rate information of the user in real time.

At operation S24, the heart rate information of the user transmitted from the wearable device is received.

At operation S25, the received heart rate information is associated (e.g., mapped) to a timeline of the user in the game.

The associating step can be implemented to integrate the heart rate information of the user to the game by, for example, mapping or projecting the heart rate information to the timeline of the game.

At operation S26, based on variations of the heart rate information associated with the timeline, the emotion fluctuations of the user are determined.

In some implementation, for example, if the heart rate within a section of the timeline, for example, a duration of time within which a game plot can be a task has been finished, increases, then the emotion of the user can be determined to be excited; if the heart rate within another section of the timeline, for example, another duration of time within which a game plot can be a fight, increases, then the emotion of the user can be determined to be nervous.

Corresponding relationships between the variations of the heart rate information associated with the timeline and the emotion fluctuations of the user can be predetermined.

At operation S27, in response to the determined emotion fluctuations of the user, one or more elements in a game scene of the game are adjusted.

Figure 3:
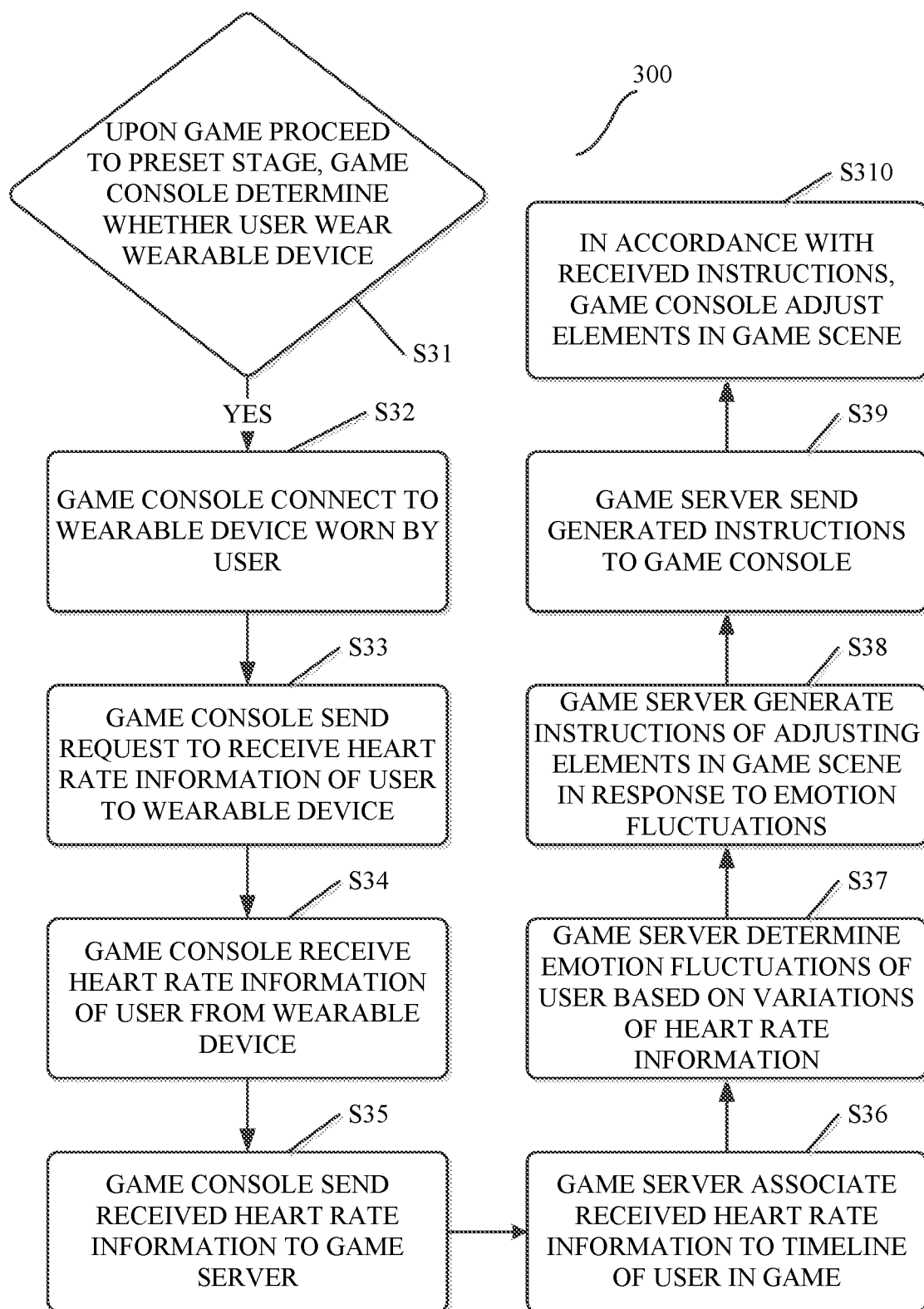
FIG. 3 is a flowchart of another example method for adjusting a game scene according to implementations of this disclosure.

FIG. 3 is a flowchart of another example method for adjusting a game scene as another example, according to implementations of this disclosure. In some implementations, the method can be implemented, by a game console (as hardware or software), or a game server, or jointly by the game console (or game software) and the game server. The method includes operations set forth in the following description as an example.

At operation S31, based on a determination that the game has proceeded to a predetermined stage, the game console determines that whether a user playing the game wears a wearable device; if the user wears the wearable device, this process proceeds to operation S32; otherwise, this process ends.

In some implementations, for example, it can be asked that whether the user wears the wearable device.

At operation S32, the game console connects to the wearable device worn by the user.

At operation S33, the game console sends a request to receive heart rate information of the user to the wearable device.

At operation S34, the game console receives the heart rate information of the user transmitted from the wearable device.

At operation S35, the game console sends the received heart rate information to the game server.

At operation S36, the game server associates the received heart rate information to a timeline of the user in the game. As will be discussed below, steps such as S36, S37, S38, S39 can also be performed at the game console, or some other device.

At operation S37, based on variations of the heart rate information associated with the timeline, the game server determines emotion fluctuations of the user.

At operation S38, in response to the determined emotion fluctuations of the user, the game server generates instructions for adjusting one or more elements in a game scene of the game.

At operation S39, the game server sends the generated instructions to the game console.

At operation S310, in accordance with the received instruction, the game console adjusts the one or more elements in the game scene of the game.

In some implementations, the method for adjusting the game scene can be implemented by a game console (as hardware or software), or a game server, or jointly by the game console (or game software) and the game server, and services such as update can be provided with flexibility. In other implementations, for example, the game can be a stand-alone game, and functions of the game server can be integrated into the game console.

Figure 4:
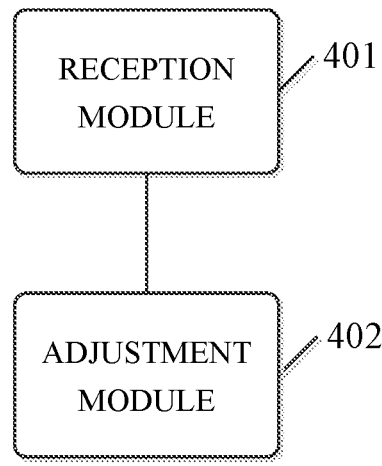
FIG. 4 is a box diagram of an example apparatus for adjusting a game scene according to implementations of this disclosure.

FIG. 4 is a box diagram of an example apparatus for adjusting a game scene according to implementations of this disclosure, including modules 401-402 set forth in the following description. The apparatus can be any computing device that can be used to play an electronic game by a user, such as a game console, a handheld game console, a remote server computer, a personal computer, a laptop computer, a tablet computer, a cell phone, a personal data assistant (PDA), or a computing service provided by a computing service provider, e.g., a website, and cloud computing. In some implementations, the computer device can include one or more components such as a processing device or a processor, a memory, a storage, an input device, an output device, a communication device, and one or more modules for specific purposes. The embodiments of the modules 401-402, 4021-4023, and 4011-4012 in this disclosure can be implemented by computer software, hardware, firmware, logic circuits (like ASIC), or their combinations.

Reception module 401 is configured to receive heart rate information acquired by a wearable device, wherein the wearable device can be used to play a game.

Adjustment module 402 is configured to, in response to the received heart rate information of the user, adjust one or more elements in a game scene of the current game played by the user.

Figure 5:
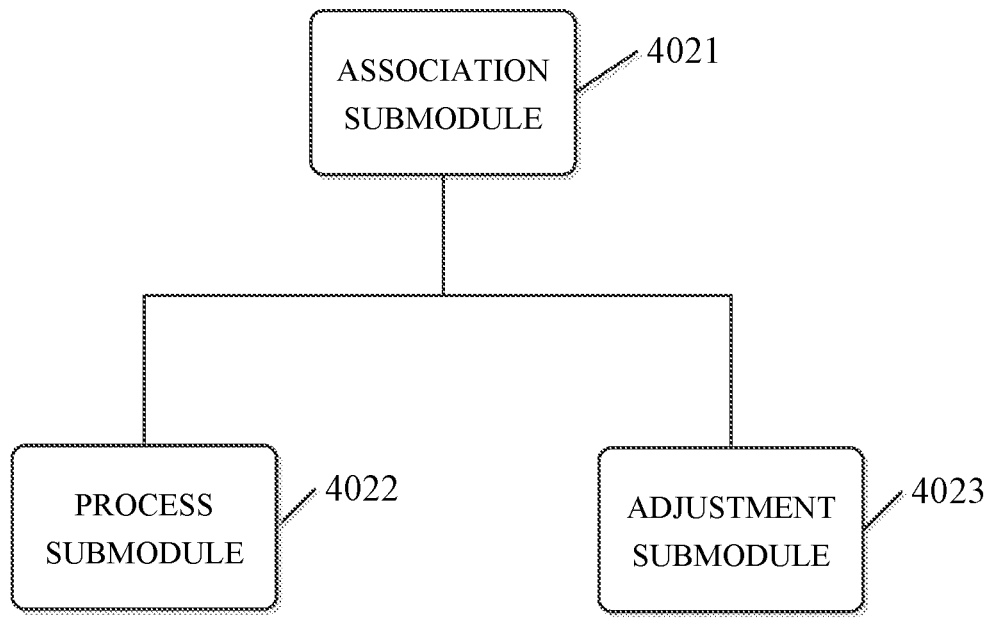
FIG. 5 is a box diagram of an example adjustment module of an apparatus for adjusting a game scene according to implementations of this disclosure.

As shown in FIG. 5, in some implementations, the foregoing adjustment module 402 further includes submodules 4021-4023 set forth in the following description.

Association submodule 4021 is configured to associate the received heart rate information to a timeline in the user in the game.

Process submodule 4022 is configured to, based on variations of the heart rate information associated with the timeline, determine emotion fluctuations of the user.

Adjustment submodule 4023 is configured to, in response to the determined emotion fluctuations of the user, adjust one or more elements in a game scene of the game.

Figure 6:
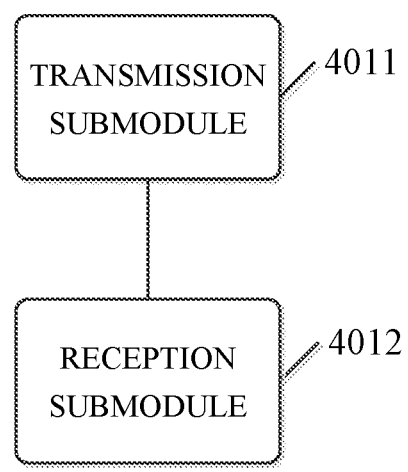
FIG. 6 is a box diagram of an example reception module of an apparatus for adjusting a game scene according to implementations of this disclosure.

As shown in FIG. 6, the foregoing reception module 401 further includes submodules 4011-4012 set forth in the following description.

Transmission submodule 4011 is configured to send a request to receive the heart rate information in the user to the wearable device.

Reception submodule 4012 is configured to receive the heart rate information of the user transmitted from the wearable device.

The foregoing submodules 4011 and 4012 can communicate (e.g., send or receive) via networks of any suitable type in any combination, including networks using Bluetooth communications, infrared communications, near field connections (NFC), wireless networks, wired networks, local area networks (LAN), wide area networks (WAN), cellular data networks and the Internet.

The foregoing reception module 401 is further configured to, based on a determination that the game has proceeded to a predetermined stage, receive the heart rate information acquired by the wearable device, wherein the user wears the wearable device to play the game.

The foregoing adjustment module 402 is further configured to, based on the received heart rate information of the user, adjust the game scene of the current game played by the user based on one or more of: a game character design, a screen background, a game plot or item purchase.

Note that, the aforementioned method for adjusting a game scene according to implementations in this disclosure is described by examples based on functions of the aforementioned modules. In practical applications, the functions can be distributed to be implemented by different functional modules based on needs, i.e., internal structures of apparatuses can be divided into different functional modules purporting to implement the foregoing functions in complete or in part. Moreover, according to implementations in this disclosure, the aforementioned methods and apparatuses for adjusting a game scene share the same conception, the specific processes for implementation of which have been described in foregoing implementations and examples, therefore will not be discussed further hereinafter.

Technical specialists skilled in the art should understand that, the implementations in this disclosure can be implemented as methods, systems, or computer program products. Therefore, this disclosure can be implemented in forms of a complete hardware implementation, a complete software implementation, and a combination of software and hardware implementation. Further, this disclosure can be embodied as a form of one or more computer program products which are embodied as computer executable program codes in computer writable storage media (including but not limited to disk storage and optical storage).

This disclosure is described in accordance with the methods, devices (systems), and flowcharts and/or block diagrams of computer program products of the implementations, which should be comprehended as each flow and/or block of the flowcharts and/or block diagrams implemented by computer program instructions, and the combinations of flows and/or blocks in the flowcharts and/or block diagrams. The computer program instructions therein can be provided to generic computers, special-purpose computers, embedded computers or other processors of programmable data processing devices to produce a machine, wherein the instructions executed by the computers or the other processors of programmable data processing devices produce an apparatus for implementing the functions designated by one or more flows in the flowcharts and/or one or more blocks in the block diagrams.

The computer program instructions can be also stored in a computer readable storage which is able to boot a computer or other programmable data processing device to a specific work mode, wherein the instructions stored in the computer readable storage produce a manufactured product containing the instruction devices which implements the functions designated by one or more flows in the flowcharts and/or one or more blocks in the block diagrams.

The computer program instructions can also be loaded to a computer or another programmable data processing device to execute a series of operating procedures in the computer or the other programmable data processing device to produce a process implemented by the computer, by which the computer program instructions executed in the computer or the other programmable data processing device provide the operating procedures for the functions designated by one or more flows in the flowcharts and/or one or more blocks in the block diagrams.

Apparently, the technical specialists skilled in the art can perform any variation and/or modification to this disclosure by the principles and within the scope of this disclosure. Therefore, if the variations and modifications herein are within the scope of the claims and other equivalent techniques herein, this disclosure intends to include the variations and modifications thereof.

What is claimed is:

1. A system for playing a game and adjusting one or more elements of a game scene within the game, the system comprising:
   a wearable device including one or more sensors for receiving heart rate information of a user while the user is playing the game;
   a game console configured for wireless communication with the wearable device, the game console including a first processor and a first memory; and
   a game server in communication with the game console, the game server including a second processor and a second memory, wherein the game is implemented using the game console and the game server,
   wherein the first processor of the game console executes instructions stored in the first memory of the game console to:
   determine whether the user is wearing the wearable device;
   responsive to a determination that the user is wearing the wearable device, establish a connection with the wearable device;
   use the connection established with the wearable device to transmit a request for the heart rate information to the wearable device;
   receive the heart rate information from the wearable device responsive to the request for the heart rate information;
   transmit the heart rate information to the game server;
   receive instructions for adjusting the one or more elements of the game scene from the game server based on the prior transmission of the heart rate information to the game server; and
   adjust the one or more elements of the game scene according to the instructions for adjusting the one or more elements of the game scene, and
   wherein the second processor of the game server executes instructions stored in the second memory of the game server to:
   receive the heart rate information from the game console;
   map the heart rate information to a timeline of the user in the game, the timeline corresponding to the game scene;
   determine one or more emotion fluctuations of the user based on variations within the heart rate information over the timeline to which the heart rate information is mapped;
   generate the instructions for adjusting the one or more elements of the game scene according to the one or more emotion fluctuations of the user; and
   transmit the instructions for adjusting the one or more elements of the game scene to the game console.

2. The system of claim 1, wherein the instructions stored in the first memory of the game console to determine whether the user is wearing the wearable device include instructions to:
   determine whether the game has proceeded to a predetermined stage; and
   responsive to a determination that the game has proceeded to the predetermined stage, determine whether the user is wearing the wearable device.

3. The system of claim 1, wherein the instructions stored in the second memory of the game server to determine the one or more emotion fluctuations of the user based on the variations within the heart rate information over the timeline to which the heart rate information is mapped include instructions to:
   determine that the heart rate information indicates a sudden acceleration of a heart rate of the user at a time of the timeline; and
   determine an emotion fluctuation of the one or more emotion fluctuations as indicating one of excitement or nervousness based on the sudden acceleration of the heart rate of the user.

4. The system of claim 1, wherein, responsive to the request for the heart rate information, the wearable device uploads the heart rate information to a storage in an accessible network, wherein the instructions stored in the first memory of the game console to receive the heart rate information from the wearable device responsive to the request for the heart rate information include instructions to:
   download the heart rate information from the storage.

5. The system of claim 1, wherein the one or more elements of the game scene include one or more of a game character design, a screen background, a game plot, or an item purchase.

6. The system of claim 1, wherein the game console is implemented in software, wherein the first processor of the game console is a first processor of the game server, wherein the first memory of the game console is a first memory of the game server.

7. The system of claim 1, wherein the wearable device is used to play the game.

8. A method for adjusting one or more elements of a game scene based on heart rate information of a user of a wearable device, the method comprising:
   determining, by a game console configured for communication with the wearable device, whether the user is wearing the wearable device, the wearable device including one or more sensors for receiving the heart rate information of the user;
   responsive to determining that the user is wearing the wearable device, causing the game console to connect to the wearable device;

using a connection established between the game console and the wearable device to transmit, from the game console, a request for the heart rate information to the wearable device;

receiving, by the game console, the heart rate information from the wearable device responsive to the request for the heart rate information;

transmitting, from the game console, the heart rate information to a game server in communication with the game console, wherein a game including the game scene is run at least in part using the game server;

mapping, by the game server, the heart rate information with a timeline of the user in the game, the timeline corresponding to the game scene;

determining, by the game server, one or more emotion fluctuations of the user based on variations within the heart rate information over the timeline to which the heart rate information is mapped;

generating, by the game server, instructions for adjusting the one or more elements of the game scene according to the one or more emotion fluctuations of the user;

receiving, by the game console, the instructions for adjusting the one or more elements of the game scene from the game server; and adjusting, by the game console, the one or more elements of the game scene according to the instructions for adjusting the one or more elements of the game scene.

9. The method of claim 8, wherein determining whether the user is wearing the wearable device comprises:

determining whether the game has proceeded to a predetermined stage; and responsive to determining that the game has proceeded to the predetermined stage, determining whether the user is wearing the wearable device.

10. The method of claim 8, wherein determining the one or more emotion fluctuations of the user based on the variations within the heart rate information over the timeline to which the heart rate information is mapped comprises:

determining, by the game server, that the heart rate information indicates a sudden acceleration of a heart rate of the user at a time of the timeline; and determining an emotion fluctuation of the one or more emotion fluctuations as indicating one of excitement or nervousness based on the sudden acceleration of the heart rate of the user.

11. The method of claim 8, wherein, responsive to the request for the heart rate information, the wearable device uploads the heart rate information to a storage in an accessible network, wherein receiving the heart rate information from the wearable device responsive to the request for the heart rate information comprises:

downloading the heart rate information from the storage.

12. The method of claim 8, wherein the one or more elements of the game scene include one or more of a game character design, a screen background, a game plot, or an item purchase.

13. The method of claim 8, wherein the game console is implemented in software.

14. The method of claim 8, wherein the wearable device is used to play the game.

* * * * *